(12) United States Patent
Traudt

(10) Patent No.: US 7,409,850 B2
(45) Date of Patent: Aug. 12, 2008

(54) SYSTEMS AND METHODS FOR MAXIMIZING HEAT TRANSFER EFFICIENCY TO AND MINIMIZING THERMAL GRADIENTS IN AN ANALYTIC COLUMN

(75) Inventor: Sammye E. Traudt, Middletown, DE (US)

(73) Assignee: Agilent Technologies, Inc, Santa Clara, CA (US)

( * ) Notice: Subject to any disclaimer, the term of this patent is extended or adjusted under 35 U.S.C. 154(b) by 0 days.

(21) Appl. No.: 11/523,180

(22) Filed: Sep. 19, 2006

(65) Prior Publication Data

US 2007/0009241 A1 Jan. 11, 2007

Related U.S. Application Data

(63) Continuation-in-part of application No. 11/434,963, filed on May 16, 2006, and a continuation-in-part of application No. 11/111,111, filed on Apr. 21, 2005, now Pat. No. 7,130,534.

(51) Int. Cl.
*G01N 30/60* (2006.01)

(52) U.S. Cl. .............................. 73/23.35; 95/82; 95/87; 96/101; 219/678; 219/679; 219/759; 392/416; 422/89

(58) Field of Classification Search ................ 73/23.35, 73/23.39; 95/82, 87; 96/101; 219/678, 679, 219/748, 759, 762; 392/416, 435; 422/89
See application file for complete search history.

(56) References Cited

U.S. PATENT DOCUMENTS

| 5,808,178 A | 9/1998 | Roundbehler et al. |
| 5,939,614 A | 8/1999 | Walters et al. |
| 6,316,759 B2 | 11/2001 | Gaisford et al. |

*Primary Examiner*—Daniel S Larkin

(57) ABSTRACT

An improved gas chromatograph system includes a radiant source, an insert located to receive an output of the radiant source, and an analytic column wound on a concave surface of the insert so that successive coils of the wound analytic column are in direct contact with each other and exert an outward pressure on the concave surface of the insert such that the outward pressure minimizes a gap between the analytic column and the concave surface of the insert so as to minimize thermal gradients and maximize heat transfer to the analytic column.

12 Claims, 14 Drawing Sheets

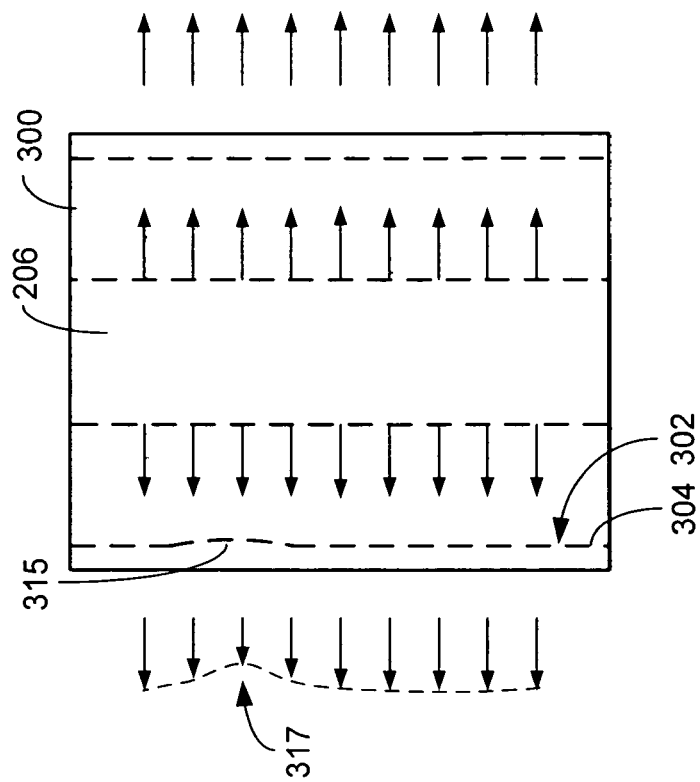
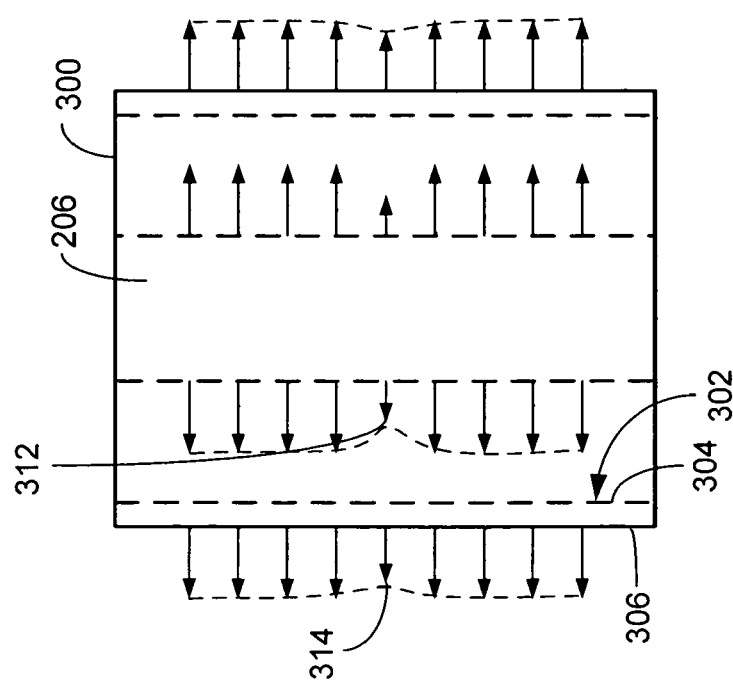
FIG. 5
FIG. 4

SYSTEMS AND METHODS FOR MAXIMIZING HEAT TRANSFER EFFICIENCY TO AND MINIMIZING THERMAL GRADIENTS IN AN ANALYTIC COLUMN

CROSS-REFERENCE TO RELATED APPLICATIONS

This application is a continuation-in-part of, commonly-assigned U.S. patent application Ser. No. 11/111,111, now U.S. Pat. No. 7,130,534 entitled "Radiant Oven For Analytic Devices," filed on Apr. 21, 2005, the entire disclosure of which is hereby incorporated into this document by reference; and is a continuation-in-part of, commonly-assigned U.S. patent application Ser. No. 11/434,963 entitled "Radiant Thermal Energy Absorbing Analytical Column," filed on May 16, 2006, the entire disclosure of which is hereby incorporated into this document by reference.

BACKGROUND

Many chemical separation analyses, such as gas and liquid chromatography, require the chemical sample to be temperature-controlled throughout the analysis. A chromatograph comprises an inlet where the sample is introduced, an oven containing an analytic column where the separation takes place, and a detector where the constituents of the sample are detected and recorded. Each of these parts of the instrument is temperature-controlled to ensure the integrity and repeatability of the analysis. An analysis performed at a constant controlled temperature is referred to as isothermal. To perform an isothermal analysis, the analytic column is typically placed in a temperature-controlled chamber, often referred to as an oven, which is preheated to the desired temperature. A non-isothermal analysis, in which the column temperature is gradually raised over time, is also common, especially for samples with relatively massive components that would otherwise take a long time to elute from the column.

Conventional chromatographic ovens typically use convection technology to heat and maintain the interior of the chamber, and hence the analytic column, at the desired temperature. However, conventional ovens are relatively large in comparison to an analytic column which they are intended to heat and, as a result, are very power inefficient. In addition to cost, a side effect of power inefficiency is that the oven is slow to heat and cool, resulting in reduced sample throughput and productivity.

Another goal when performing a chromatographic analysis is to quickly heat the analytic column to the desired temperature. The use of radiant sources to heat the analytic column is becoming more widespread. A factor to consider when using a radiant source to heat the analytic column is the directionality of the radiant energy provided by the radiant source. For example, light waves are directional so that the line-of-sight between the source and the analytic column is a consideration. Another factor to consider when implementing a radiant source is the phenomenon of thermal gradients, which may result in uneven heating of the analytic column.

Therefore, it would be desirable to maximize heat transfer between a radiant energy source and an analytic column. Further, it is desirable to minimize thermal gradients in an analytic column.

SUMMARY OF INVENTION

In accordance with an embodiment, a gas chromatography system includes a radiant source, an insert located to receive an output of the radiant source, and an analytic column wound on a concave surface of the insert so that successive coils of the wound analytical column are in direct contact with each other and exert an outward pressure on the concave surface of the insert such that the outward pressure minimizes a gap between the analytic column and the concave surface of the insert so as to minimize thermal gradients and maximize heat transfer to the analytic column.

According to another embodiment, a gas chromatography system includes an oven and a radiant source configured to provide radiant energy, and an analytic column located proximate to the radiant source. The radiant source has a structure configured to vary an output of the radiant source so that thermal energy imparted to the analytical column is varied to compensate for the temperature variation over the analytical column.

Other embodiments and methods of the invention will be discussed with reference to the figures and to the detailed description.

BRIEF DESCRIPTION OF THE FIGURES

The invention will be described by way of example, in the description of exemplary embodiments, with particular reference to the accompanying figures.

FIG. 4 is a side view of the insert and radiant source illustrating an energy gradient caused by the radiant source.

FIG. 5 is a side view of the insert and radiant source illustrating an energy gradient caused by the insert.

DETAILED DESCRIPTION

While described below for use in a gas chromatograph using a thermal radiation source, the structure and techniques described below can be used in an analytic oven that uses another electromagnetic (EM) source, such as a microwave source and a radio frequency (RF) energy source. The structure and techniques described below are also applicable to liquid chromatography. The structure and techniques described below generally describe a wound analytic column coated to absorb radiation or an insert coated to absorb radiation onto which or within which an analytic column is wound. However, any target configured to receive radiation can be used.

Figure 1:
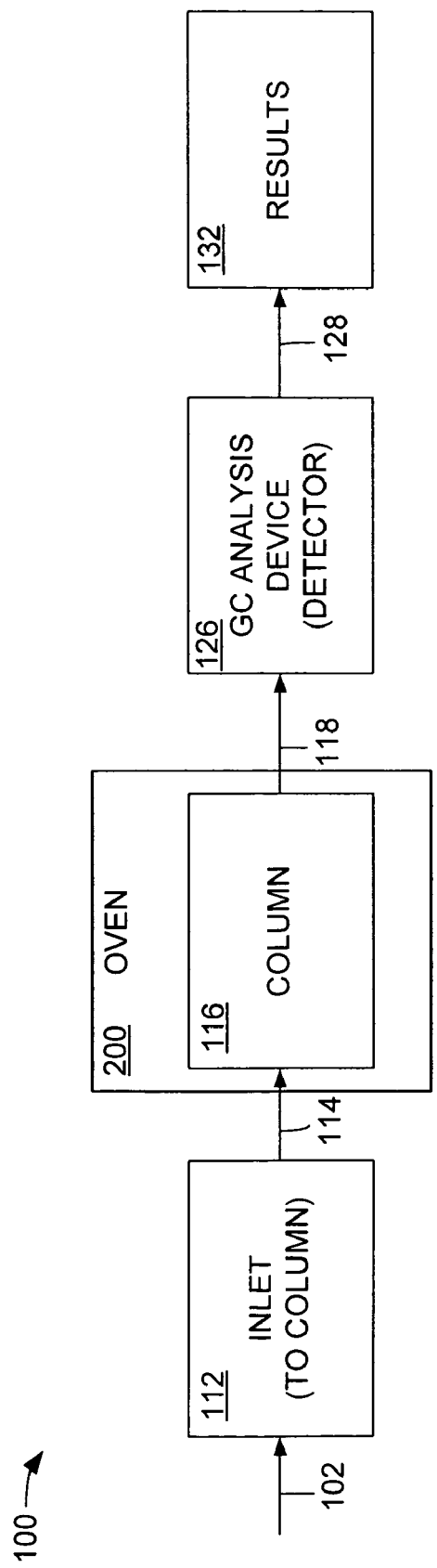
FIG. 1 is a schematic diagram illustrating a simplified chromatograph.

FIG. 1 is a block diagram illustrating a simplified gas chromatograph 100, which is one possible device in which the systems and methods for maximizing heat transfer efficiency to and minimizing thermal gradients in an analytic column may be implemented.

The gas chromatograph 100 includes an inlet 112, which receives a sample of material to be analyzed via connection 102 and provides the sample via connection 114 to, for example, an analytic column 116. In this example, the analytic column 116 is a chromatographic column, and is also referred to as a capillary column, or just a column. To effectively separate compounds of interest during chromatography, the analytic column 116 may be heated to temperatures well above ambient temperature. The temperature to which the analytic column 116 is heated is dependent on the type of sample being analyzed and may vary during a sample run to analyze multiple compounds and elements from a single sample. Accordingly, the analytic column 116 is located in a temperature chamber, also referred to as an oven 200. In this example, the oven 200 is a radiant oven that provides radiant energy from a radiant energy source.

The output of the analytic column 116 is connected via connection 118 to a detector 126. The output of the detector 126, via connection 128, is a signal representing the result 132 of the analysis.

In an embodiment, a gas chromatograph system comprises a radiant source, an insert located to receive an output of the radiant source, and an analytic column wound on a concave surface of the insert. In this embodiment, successive coils of the wound analytic column are in direct contact with each other and exert an outward pressure on the concave surface of the insert such that the outward pressure minimizes a gap between the analytic column and the concave surface of the insert. The successive coils insulate each other. This arrangement minimizes thermal gradients and maximizes heat transfer to the analytic column. The analytic column may include a coating that is absorptive of the energy emitted from the radiant source. The coating may be of uniform or varying thickness. The insert may also include a coating of uniform or varying thickness. The coating on the analytic column and the insert compensates for temperature variation over the analytic column caused by natural convection.

In an embodiment, the radiant source has a shape that approximates the shape of the analytic column. In another embodiment, the analytic column is wound into a shape in which the dimension of the wound analytic column in the direction of gravity is the smallest dimension of the wound analytic column. In another embodiment, the radiant source comprises a structure configured to vary an output of the radiant source so that thermal energy imparted to the analytic column is varied to compensate for the temperature variation over the analytic column caused by natural convection.

In another embodiment, a light diffuser is located between the radiant source and the analytic column. In another embodiment, a filament in the radiant source, is symmetrical with respect to the shape of the radiant source. In another embodiment, the radiant source provides a radiation pattern and the analytic column is located proximate to the radiation pattern so that an angle of incidence with respect to the radiation pattern and the analytic column is consistent to maximize absorption of radiant energy emitted from the radiant source.

In another embodiment, the system includes an oven in which an interior surface of the oven comprises reflective material configured to redirect stray radiant energy back to the radiant source.

Figure 2A:
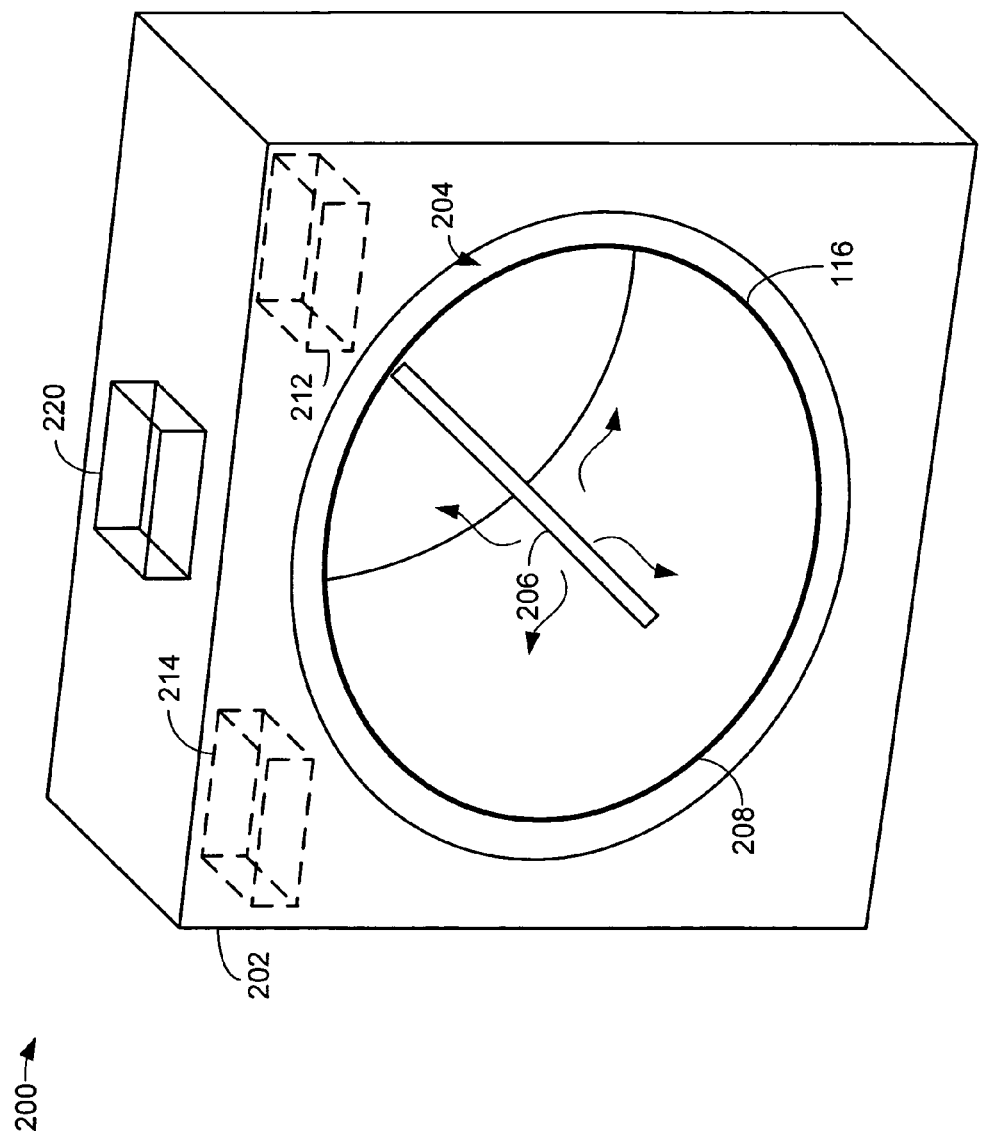
FIG. 2A is a schematic diagram illustrating a perspective view of an embodiment of the radiant oven and analytic column of FIG. 1.

FIG. 2A is a schematic diagram illustrating a perspective view of an embodiment of the radiant oven 200 and analytical column 116 of FIG. 1. The radiant oven 200 includes a housing 202 having a recess 204. The recess 204 is configured to releasably receive an analytic column 116. The analytic column 116, which in this example is a chromatographic column, is coiled and placed in the recess 204. In an embodiment, the analytic column 116 is coated with a material that efficiently absorbs radiant energy and converts the radiant energy to heat. Embodiments of the analytic column 116 will be described in detail below. The analytic column 116 can be either tightly or loosely coiled, depending on application. The input and output of the analytic column 116 is omitted for drawing clarity. A temperature sensor 208 can be secured to the analytic column 116 to precisely determine the temperature of the analytic column 116. In an embodiment, the temperature sensor 208 is coated with the same material with which the analytic column 116 is coated and placed in the radiant oven 200 at approximately the same distance from the radiant source as the analytic column 116. In this way, the temperature sensor 208 is heated in the same manner as the analytic column 116.

The oven 200 also includes a radiant source 206 and control circuitry 212 configured to control the duty cycle of the power supplied to the radiant source 206. The control circuitry 212 uses information fed back from the temperature sensor 208 to determine the power required to achieve and maintain the temperature in the radiant oven 200 at a set point prescribed by the analysis. The duty cycle is the fraction of ON time of the radiant source relative to the total cycle (ON+ OFF) time. In addition to controlling the duty cycle of the radiant source 206 it is often important to control the total cycle time as well. For example, a duty cycle of 20% can be achieved with an ON time of 2 minutes vs. a total time of 10 minutes or an ON time of 2 seconds vs. a total time of 10 seconds, etc. Although the duty cycle is the same, the total cycle times can be quite different. The total cycle time (10 minutes, 10 seconds, 10 milliseconds, etc.) plays an important role for radiant sources having fast reaction times such as a quartz halogen infrared (IR) radiant source. When the total cycle time is too long for a quartz halogen IR radiant source, the filament can cool significantly between cycles. Repeated heating and cooling of the filament in a quartz halogen IR radiant source causes fatigue and shortens the life of the filament. Many quartz halogen radiant source manufacturers suggest using "phase-angle fired" control where the total cycle time can be as small as a fraction of one cycle of the AC input power.

In an embodiment and as will be described further below, the radiant source 206 has an elongate shape, the length of which approximates the coiled height of the analytic column 116. Matching the shape of the radiant source 206 to the dimension of the analytic column 116 helps to maintain even heating of the analytic column 116.

The radiant oven 200 optionally includes a fan 214, or other means for quickly cooling the oven 200. In an embodiment, the radiant source 206 is a quartz halogen IR bulb having a cylindrical profile. However, the shape of the radiant source 206 may differ. The radiant source can be an infrared (IR) source as mentioned above, a microwave source, an ultraviolet (UV) source, a visible (VIS) source, an X-ray source, an RF source or any other electromagnetic (EM) radiant source. In addition, the radiant source 206 may be one that emits radiant EM energy at multiple wavelengths, one that emits radiant EM energy at a single wavelength, such as a laser, and one that emits both visible and invisible IR, UV, or any combination thereof. A cover is omitted from the radiant oven 200 for clarity. In an embodiment, the radiant oven 200 includes a sealed cover and is coupled to a vacuum source 220 so that a vacuum can be drawn in the recess 204 containing the analytic column 116 and the radiant source 206.

The analytic column 116 is fabricated from fused silica glass, which is transparent to visible wavelengths of EM energy. Visible wavelengths of EM energy are desirable because they are high energy. Visible (VIS) light has a wavelength that ranges from approximately 400 nanometers (nm) to 700 nm. Infrared (IR) radiation ranges in wavelength from approximately $0.01\text{-}7 \times 10^{-5}$ centimeters; and ultraviolet (UV) radiation ranges in wavelength from approximately $4 \times 10^{-5}$-$10^{-7}$ centimeters. In an embodiment, and as will be described in detail below, the analytic column 116 is coated with a material that exhibits a high solar absorbance at the wavelength or wavelengths of the output of the radiant source 206 including the desirable visible region. In an embodiment, the analytic column 116 is coated with a material that exhibits a high solar absorbance at ultraviolet (UV) and visible (VIS) wavelengths and converts the radiant energy into heat. Solar absorptivity, denoted $\alpha$, is the fraction of incoming light that is absorbed by the material and consequently converted to heat. Solar absorptivity is not only material-dependent but also dependent on wavelength ($\lambda$) and incidence angle ($\theta$) of the incident light (i.e., $\alpha = \alpha_{\lambda,\theta}$). However, for practicality and often as a good approximation, $\alpha$ is most often quoted as a single value representing an average over all wavelengths (or a subset of wavelengths, such as the wavelengths of UV, VIS, or IR) and incidence angles. Values generally range from 0 to 1 with a high value generally of 0.85 or greater. The coating on the analytic column 116 converts the radiant EM energy to heat. The heat is transmitted via conduction directly to the analytic column 116.

Figure 2B:
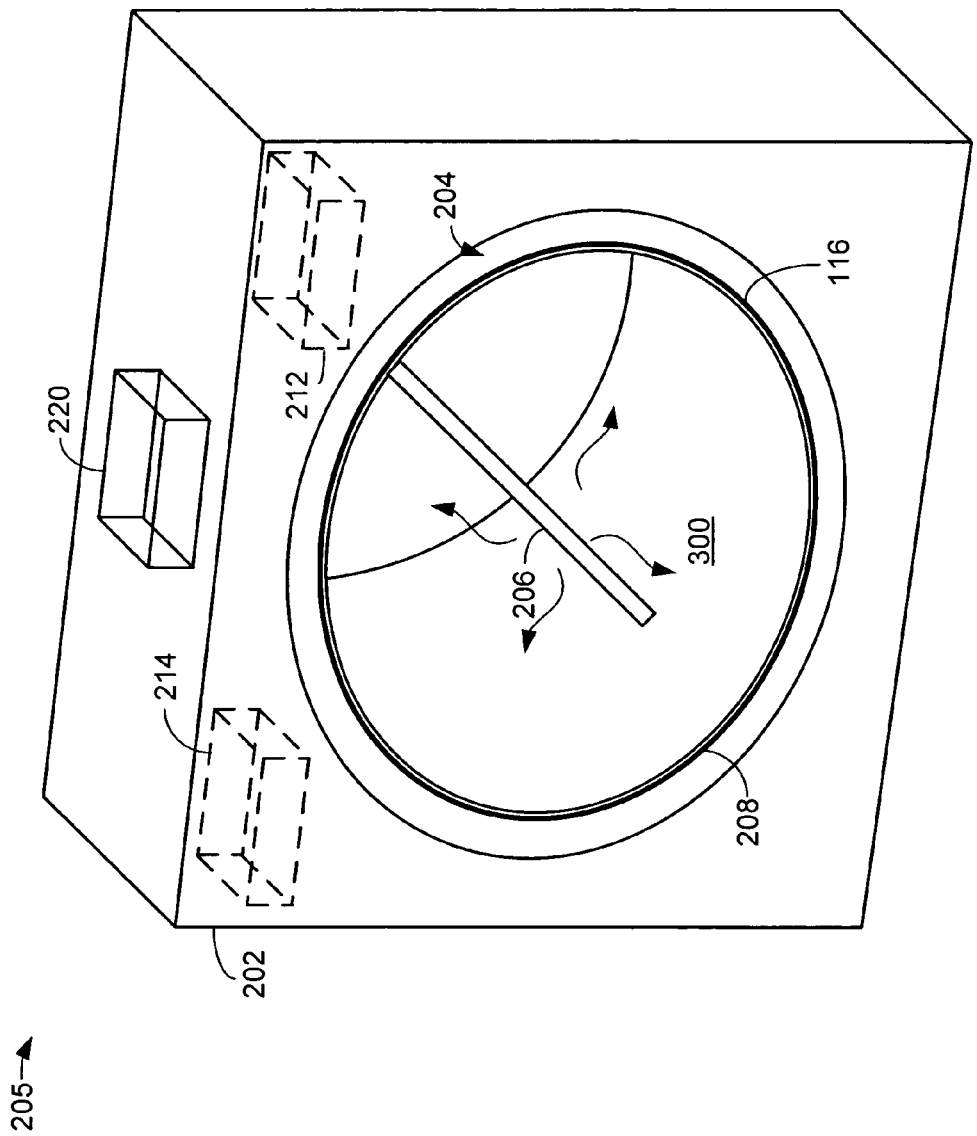
FIG. 2B is a schematic diagram illustrating a perspective view of an embodiment of the radiant oven and analytic column of FIG. 1 including an insert.

FIG. 2B is a schematic diagram illustrating a perspective view of an embodiment of the radiant oven 200 of FIG. 1 including an insert 300. The radiant oven 205 is similar to the radiant oven 200 described in FIG. 2A. The radiant oven 205 in FIG. 2B includes a recess 204 that is configured to releasably receive an insert 300. The insert 300 is also sometimes referred to as a basket. The analytic column 116, which in this example is a chromatographic column, is wrapped around the insert 300 or is coiled inside the insert 300 so that the analytic column 116 can be efficiently and uniformly heated and cooled in the oven 200. To maintain even heating, the analytic column 116 is tightly wrapped around the outer surface of the insert 300 or inside the insert 300, depending on application. In an embodiment, the analytic column 116 is tightly wrapped inside or around the outside of the insert 300 to minimize the amount of exposed column surface area so that heat absorption is maximized. The input and output of the analytic column 116 is omitted for drawing clarity. In an embodiment, the analytic column 116 is wound on a concave surface of the insert 300 so that successive coils of the wound analytic column 113 are in direct contact with each other and exert an outward pressure on the concave surface of the insert 300 such that the outward pressure minimizes a gap between the analytic column 116 and the concave surface of the insert 300 so as to minimize thermal gradients and maximize heat transfer to the analytic column 116.

Figure 3B:
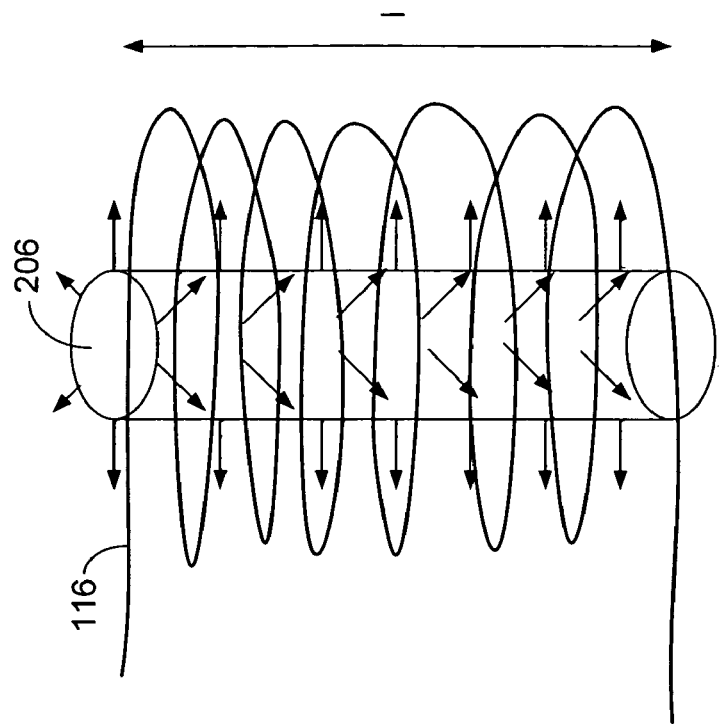
FIG. 3B is a schematic diagram illustrating matching the shape and dimension of the radiant source to the shape and dimension of the analytic column.
Figure 3A:
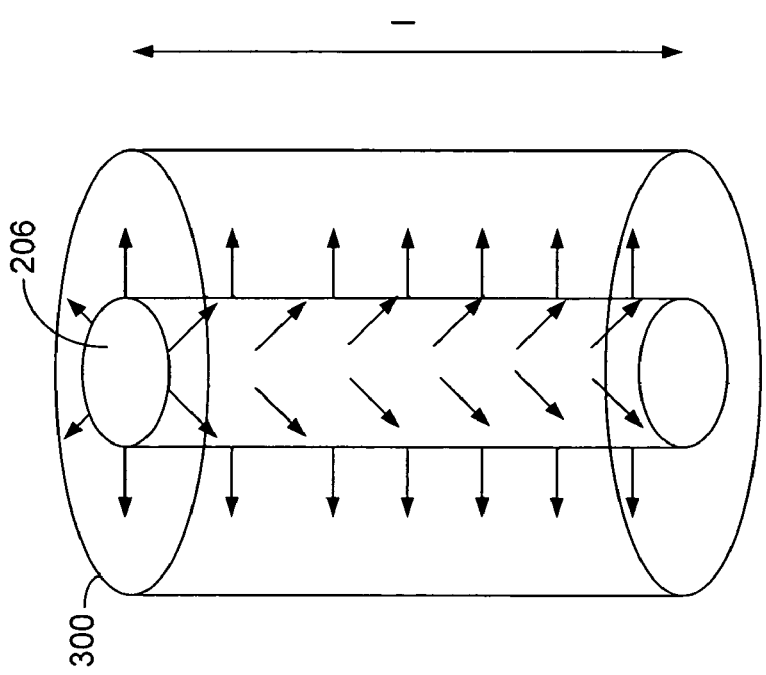
FIG. 3A is a schematic diagram illustrating matching the shape and dimension of the radiant source to the shape and dimension of the insert.

FIG. 3A is a schematic diagram illustrating matching the shape and longitudinal dimension of the radiant source 206 to the shape and longitudinal dimension of the insert 300. In this example, the radiant source has a cylindrical shape that has a longitudinal dimension, l that approximates the longitudinal dimension, l of the cylindrical shape of the insert 300.

FIG. 3B is a schematic diagram illustrating matching the shape and longitudinal dimension of the radiant source 206 to the shape and longitudinal dimension of the analytic column 116. In this example, analytic column 116 is wound as a general helix shape that includes a longitudinal dimension, l that approximates the longitudinal dimension, l of the radiant source 206.

FIG. 4 is a side view of the insert 300 and radiant source 206 illustrating an energy gradient caused by the source 206. In this example, the radiant source 206 has an imperfection that results in an energy gradient in the output of the radiant source 206. The energy gradient is illustrated using the arrow 312. In an embodiment, the insert 300 can be fabricated using aluminum, or another material having good thermal conduction properties. The aluminum can be black anodized resulting in a coating 302 that exhibits high thermal absorption characteristics. In the example shown in FIG. 4, the radiant energy from the radiant source 206 irradiates the inner surface 304 of the insert 300 resulting in heating of the insert 300 where the heat is conducted to and is absorbed by the coating 302. The inner surface 304 is a concave surface. As the heat travels through the thickness of the insert 300 (in the direction of the arrows), it also travels along the surface of the insert 300 due to the high conductivity of the base material, which in this example is aluminum. The aluminum absorbs the heat and reduces the energy gradient 312 at the surface 306 of the insert 300 illustrated using arrow 314. The wall of the insert 300 can be, for example, 1-2 millimeters (mm) thick and the coating 302 is approximately 20-50 micrometers (μm) thick. The analytic column 116 can be wrapped around the insert 300 or can be coiled and inserted inside the insert 300.

FIG. 5 is a side view of the insert 300 and radiant source 206 illustrating an energy gradient caused by the insert 300. An imperfection 315 in the coating 302 can cause an energy gradient at the outer surface 306 of the insert 300. The energy gradient is illustrated using arrow 317. The energy gradient 317 can be minimized by making the thickness of the coating 302 as consistent as possible over the entire inner surface 304 of the insert 300.

Figure 6:
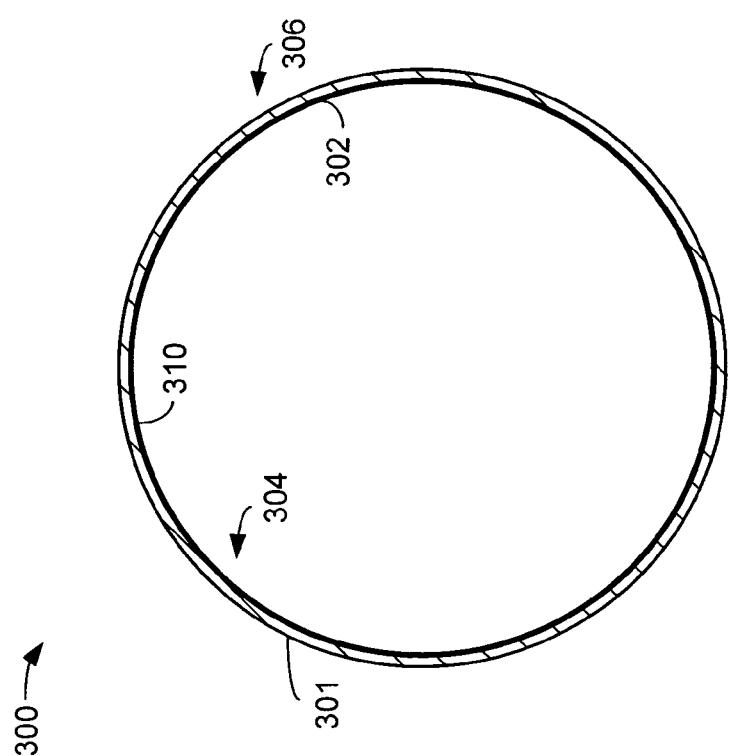
FIG. 6 is a schematic diagrams illustrating a plan view of an embodiment of the insert of FIG. 2B.

FIG. 6 is a schematic diagram illustrating a plan view of an embodiment of the insert of FIG. 2B. The insert 300 comprises a body 301 that can be fabricated from an efficient heat conductive material, such as, for example, aluminum or copper. The insert 300 comprises an inner surface 304 and an outer surface 306. In one embodiment, the insert 300 is aluminum and the inner surface 304 is anodized to form a dark, and preferably black, surface coating 302. The surface coating 302 can be of a uniform thickness or can be of varying thickness. The inner surface 304 is configured to absorb the radiant EM energy emitted by the radiant source 206 and convert the radiant EM energy to heat. The heat is conducted through the wall between the inner surface 304 and the outer surface 306. As described above, an analytic column 116 is either in direct contact with or in close proximity to the outer surface 306. In this manner, heat from the outer surface 306 is coupled, either via conduction or convection, to the analytic column 116. The dark inner surface 304 can alternatively have another coating 310 with a property that allows it to absorb the radiant EM energy emitted by the radiant source 206 and convert the radiant EM energy to heat.

Figure 7A:
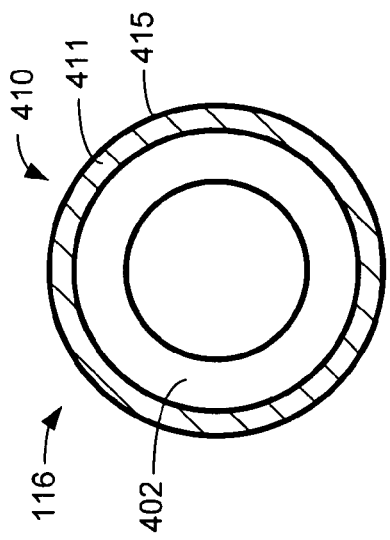
FIG. 7A is a schematic diagram illustrating a cross-sectional view of an embodiment of the analytic column of FIG. 3B.

FIG. 7A is a schematic diagram illustrating a cross-sectional view of an embodiment of the analytic column 116 of FIG. 3B. The analytic column 116 comprises a wall 402 that defines an inner diameter of the analytic column 116 and a coating 410. The wall is typically fabricated from fused silica, or a similar material. The coating 410 is a material that exhibits a high solar absorbance, referred to as $\alpha$, at the wavelength of the output of the radiant source 206. In an embodiment, the coating 410 is formed to a uniform thickness from a material such as polyimide into which a material that exhibits high solar absorbance has been added. Alternatively, the thickness of the coating 410 can vary over the analytic column 116 to compensate for temperature variation over the analytic column caused by natural convection. For example, the coating 410 can be one or more layers of polyimide including carbon black. In an embodiment, the polyimide is absorbent of the IR energy and the carbon black enhances the absorption of the visible (VIS) light, which is higher in energy than the IR light. The combination of the polyimide and the carbon black absorb the IR and the VIS energy emitted by the radiant source 206 (FIGS. 2A and 2B) and efficiently convert the radiant energy to heat.

In an embodiment, a fused silica column having an inner diameter (ID) of 320 micrometers (μm) and an outer diameter (OD) of 445 μm is coated with a base coating 411 of several layers of polyimide totaling approximately 18-20 μm thick. Then a final coating 415 of polyimide impregnated with approximately 1-2% carbon black approximately 4-5 μm thick is applied over the polyimide. The final coating 415 of polyimide and carbon black absorbs the UV or VIS light, converts the UV or VIS light to heat and efficiently transfers the heat to the wall 402 of the analytic column 116.

In another embodiment, a significantly thicker initial coating of polyimide, approximately 35 to 40 μm thick, is applied to the wall 402 of the analytic column 116. At sufficient thickness, the relatively thick coating of polyimide will become opaque to visible light and will efficiently convert the radiant energy to heat without the carbon black polyimide layer.

Figure 7B:
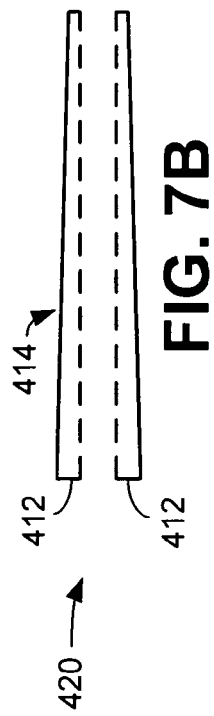
FIG. 7B is a schematic diagram illustrating a cross-sectional view of an alternative embodiment of the analytic column of FIG. 3B.

FIG. 7B is a schematic diagram illustrating a cross-sectional view of an alternative embodiment of the analytic column 116 of FIG. 3B. The analytic column 420 includes a wall 412 that varies in thickness along the length of the analytic column 420. The analytic column 420 also has a nominal polyimide coating 414 approximately 10 to 30 μm thick, having a consistent thickness. As will be described in detail below, the wall 420 of varying thickness absorbs radiant energy at a different rate along its length and can be used to minimize the effect of natural convection and equalize the temperature of the analytic column 420 in the direction of gravity.

Figure 7C:
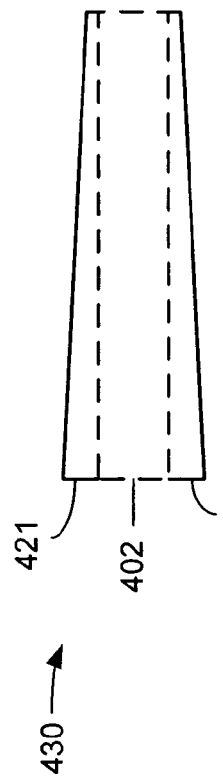
FIG. 7C is a schematic diagram illustrating a cross-sectional view of another alternative embodiment of the analytic column of FIG. 3B.

FIG. 7C is a schematic diagram illustrating a cross-sectional view of another alternative embodiment of the analytic column 116 of FIG. 3B. The analytic column 430 includes a coating 421 that varies in thickness along the length of the analytic column 430. As will be described in detail below, the coating 421 of varying thickness absorbs radiant energy at a different rate along its length and can be used to minimize the effect of natural convection and equalize the temperature of the analytic column 430 in the direction of gravity. The embodiments of the analytic column 420 in FIG. 7B and the analytic column 430 in FIG. 7C can be combined to result in an analytic column having a varying wall thickness and a varying coating thickness.

Figure 8:
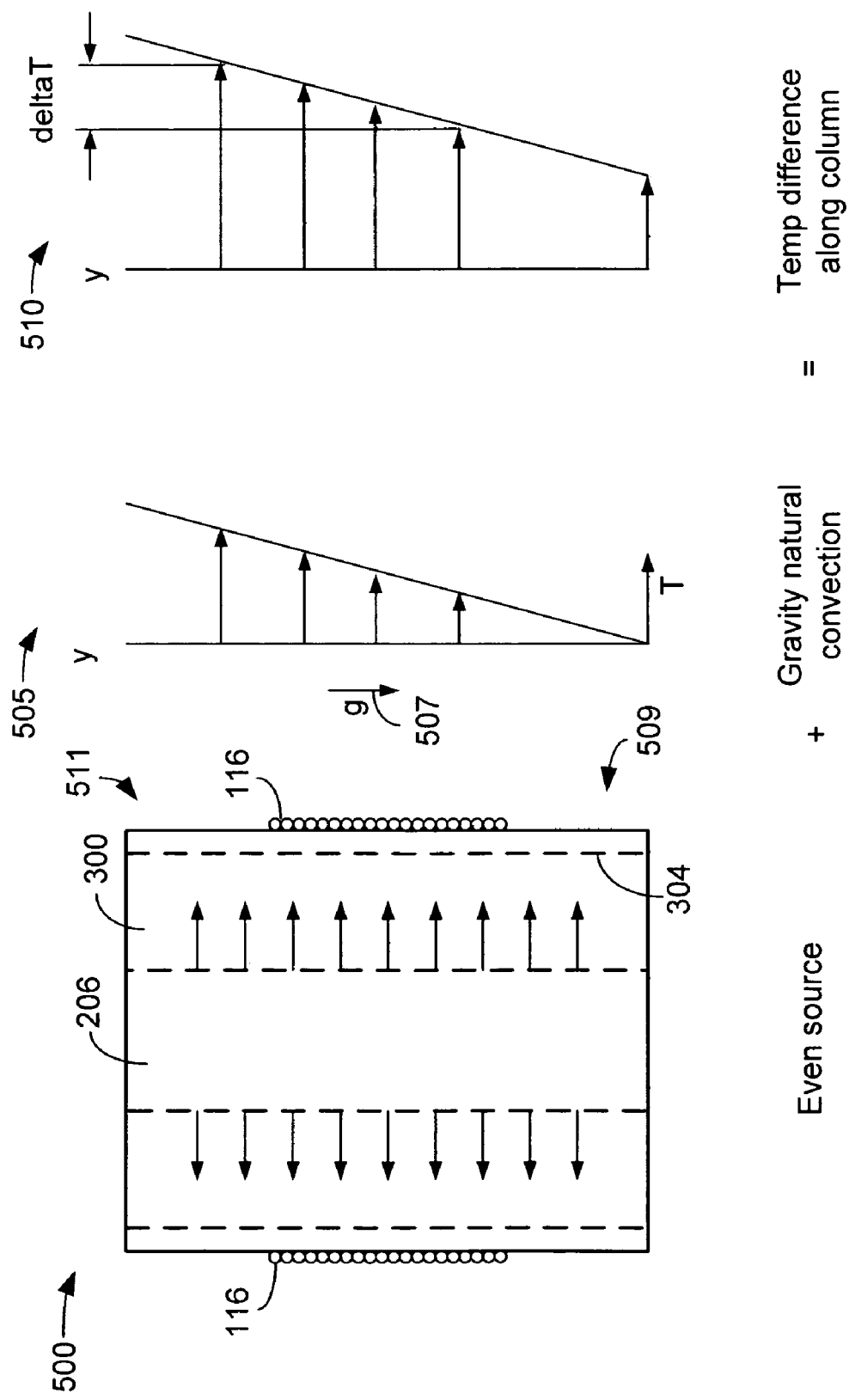
FIG. 8 is a schematic diagram illustrating the effect of natural convection on the transfer and absorption of energy in an analytic column.

FIG. 8 is a schematic diagram 500 illustrating the effect of natural convection on the transfer and absorption of energy in an analytic column. In this example, the radiant source 206 emits a consistent amount of radiant energy along the length of the radiant source 206. The graph 505 illustrates that when the direction of gravity is indicated by the arrow 507, the amount of energy impinging on the surface 304 is reduced toward the bottom 509 as a result of natural convection. Gravity causes a gradient in fluids that is referred to as "natural convection," in which a hotter fluid will rise relative to a cooler fluid. The graph 510 illustrates that there will be a temperature differential, referred to as $\Delta T$, along the analytic column 116 and in the insert 300 along the direction of gravity, g. Related to the graphs 505 and 510, it holds that there will be more heat delivered to the upper portion 511 of the insert 300 than to the lower portion 509 of the insert 300. One way to minimize this effect is to minimize the dimension of the insert and analytic column, or just the analytic column if no insert is used, in the direction of gravity, g, so that the dimension of the analytic column in the direction of gravity is the smallest dimension of the wound analytic column. For example, if the analytic column 116 is wound around, or inside, the insert 300, the major axis of which is in the direction of gravity, g, then it is preferable that the height of the insert and/or the wound column be minimized. In this example, the major axis of the insert 300 and the wound column 116 is along the direction of gravity, g.

Figure 9:
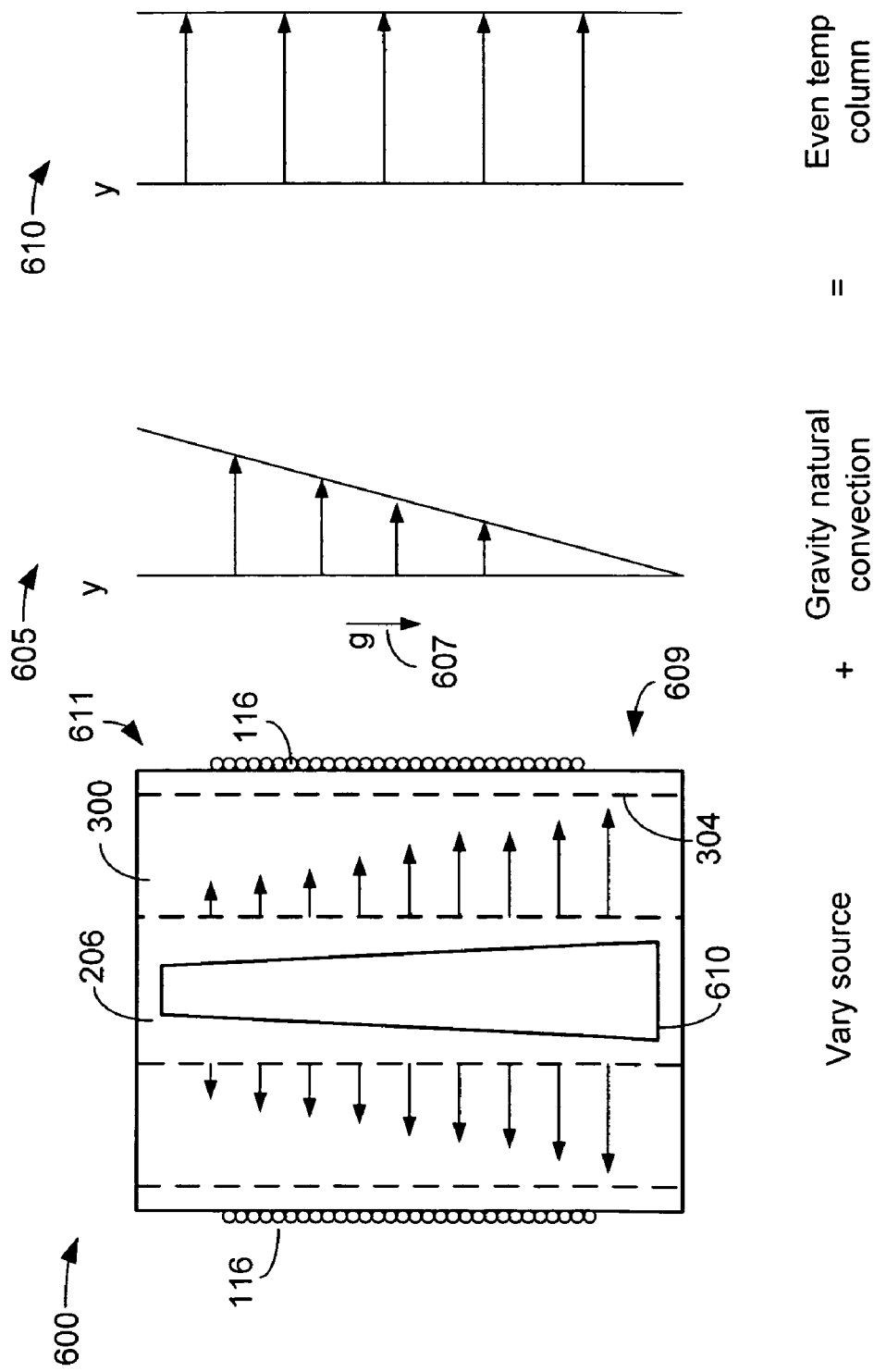
FIG. 9 is a schematic diagram illustrating an embodiment of a way of compensating for the effect of natural convection on the transfer and absorption of energy in an analytic column.

FIG. 9 is a schematic diagram 600 illustrating an embodiment of a way of compensating for the effect of natural convection on the transfer and absorption of energy in an analytic column. In FIG. 9, the output of the radiant source 206 varies along the major axis of the radiant source 206 so that more radiant energy is emitted toward the bottom portion 609 of the insert 300 than toward the upper portion 611 of the insert 300. For example, a radiant source 206 that outputs radiant energy at different levels over the source can be formed using a filament 610 the thickness of which varies along the length of the filament 610. When coupled with the effect of natural convention as illustrated in graph 605, the temperature along the analytic column 116 is equalized along the direction of gravity 607, as illustrated using graph 610. Varying the output of the radiant source 206 along its longitudinal direction also has the effect of equalizing the temperature of the analytic column 116 in the absence of the insert 300. The radiant source 206 includes a structure configured to vary an output of the radiant source 206 so that thermal energy imparted to the analytic column 116 is varied to compensate for the temperature variation over the analytic column 116.

Figure 10:
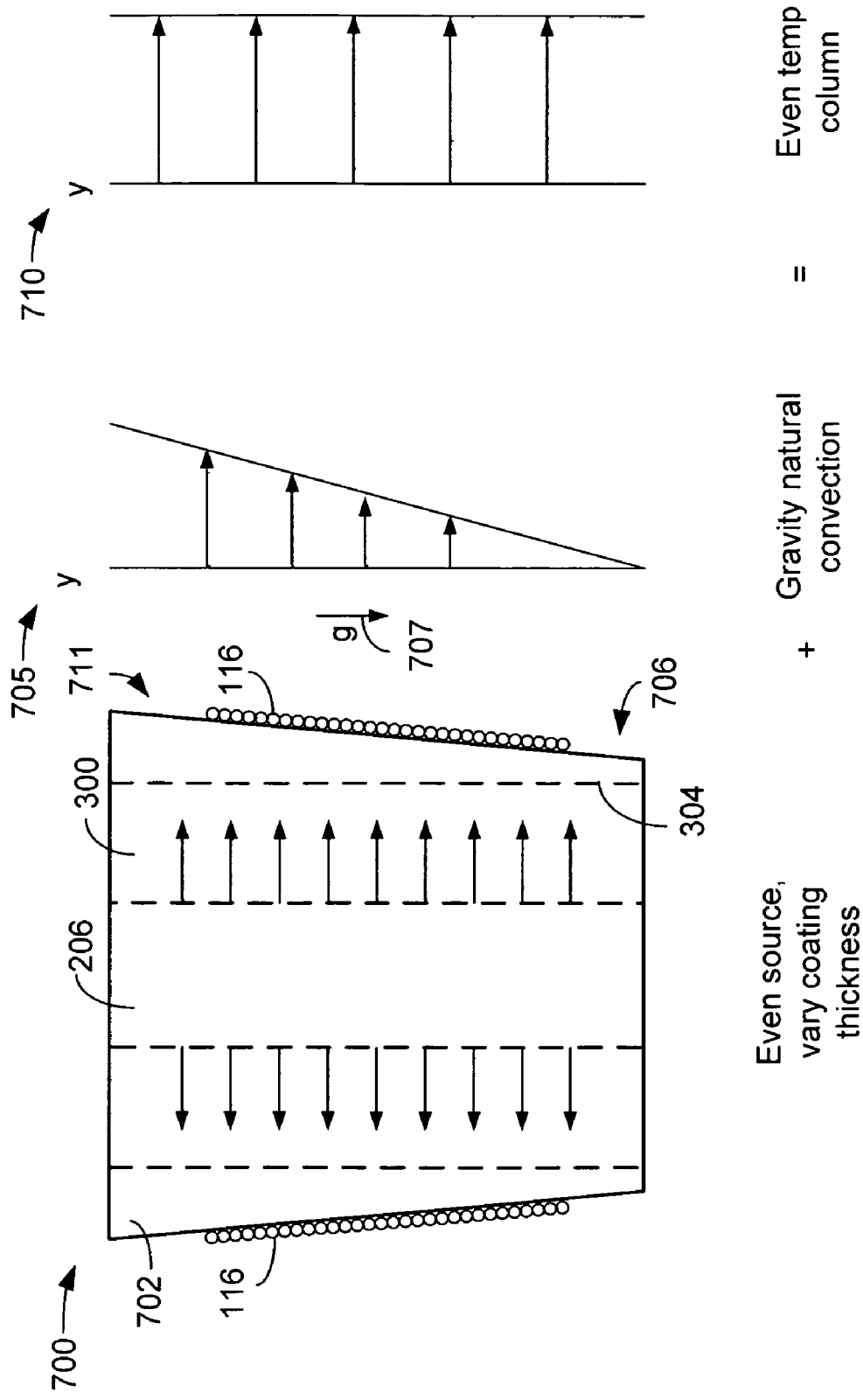
FIG. 10 is a schematic diagram illustrating an alternative embodiment of a way of compensating for the effect of natural convection on the transfer and absorption of energy in an analytic column.

FIG. 10 is a schematic diagram illustrating an alternative embodiment of a way of compensating for the effect of natural convection on the transfer and absorption of energy in an analytic column. In FIG. 10, the output of the radiant source 206 is constant along its length and the thickness of the coating 702 is varied along the major axis of the insert 300 so that more radiant energy is absorbed by the coating toward the upper portion 711 of the insert 300 than toward the lower portion 706 of the insert 300. Alternatively, in the absence of the insert 300, the thickness of the analytic column 116 and/or the coating applied to the analytic column 116 can be varied as shown in FIGS. 7B and 7C. When coupled with the effect of natural convention as illustrated in graph 705, the temperature along the analytic column 116 is equalized along the direction of gravity, as illustrated using graph 710. Varying the thickness of the coating 702, varying the wall thickness of the analytic column 116 along its longitudinal direction, and/or varying the thickness of the coating on the analytic column 116 also has the effect of equalizing the temperature of the analytic column 116 and can be used singly or in combination to counteract the effect of natural convection.

Figure 11:
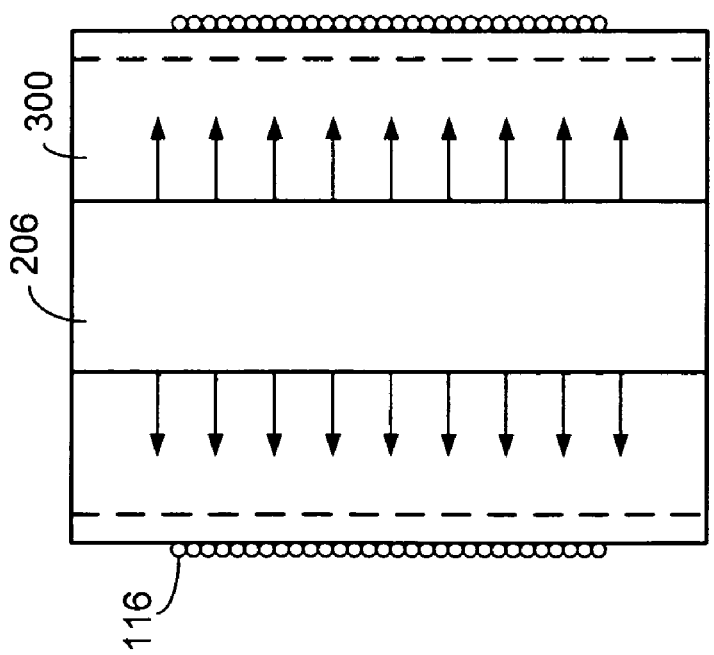
FIG. 11 is a schematic diagram illustrating an analytic column tightly wound around an insert.

FIG. 11 is a schematic diagram illustrating an analytic column 116 tightly wound around an insert 300. When using an insert 300, closely winding the analytic column 116 around the insert 300 ensures that the temperature of the analytic column 116 will closely follow the temperature of the insert 300. Gaps between the analytic column 116 and the insert 300, or gaps between the coils of the analytic column 116, will slow heating by introducing additional resistance to conduction.

Figure 12:
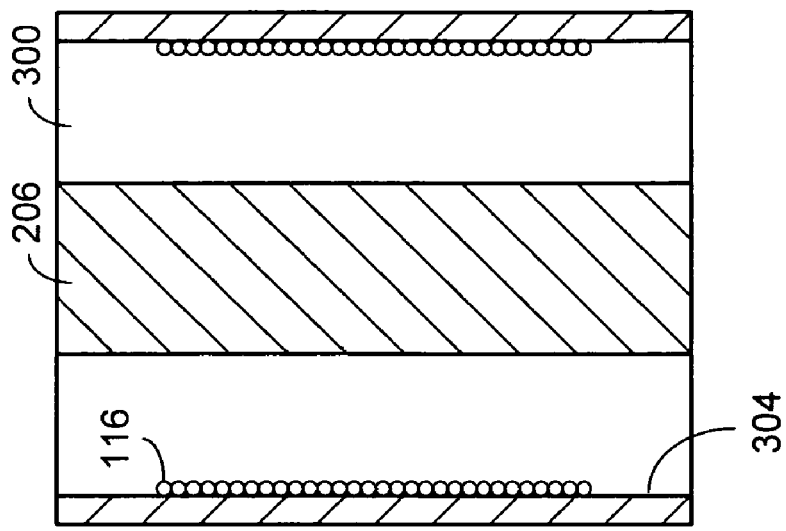
FIG. 12 is a cross-sectional schematic diagram illustrating an analytic column tightly wound inside an insert.

FIG. 12 is a cross-sectional schematic diagram illustrating an analytic column 116 tightly wound inside an insert 300. When using an insert 300, closely winding the analytic column 116 around the insert 300 dictates that the natural tension or "springiness" of the analytic column 116 be overcome. In FIG. 12, the analytic column 116 is tightly wound inside the insert 300. It this manner, the natural tension of the analytic column 116 provides an outward pressure that is advantageously used to keep the column close to the concave inner surface 304 of the insert 300. Further, the successive coils of the column are in direct contact with each other to help thermally insulate each other.

Figure 13:
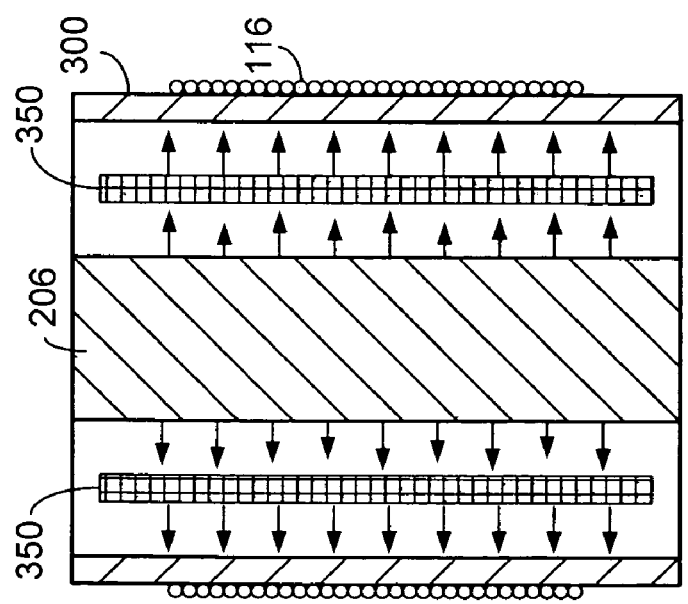
FIG. 13 is a cross-sectional schematic diagram illustrating the use of a light diffuser between the radiant source and the analytic column.

FIG. 13 is a cross-sectional schematic diagram illustrating the use of a light diffuser between the radiant source 206 and the analytic column 116. Minor gradients in the output of the radiant source 206 can be reduced by implementing a light diffuser 350 between the radiant source 206 and the analytic column 116. The example shown in FIG. 13 includes an insert 300. However, the insert 300 may be omitted. The light diffuser 350 randomizes the direction of the radiant energy by introducing random surfaces to transmit and refract the light emitted by the radiant source 206. A diffuser 350 contains a number of randomly oriented small surfaces that randomly redirect the light from the radiant source 206.

Figure 14:
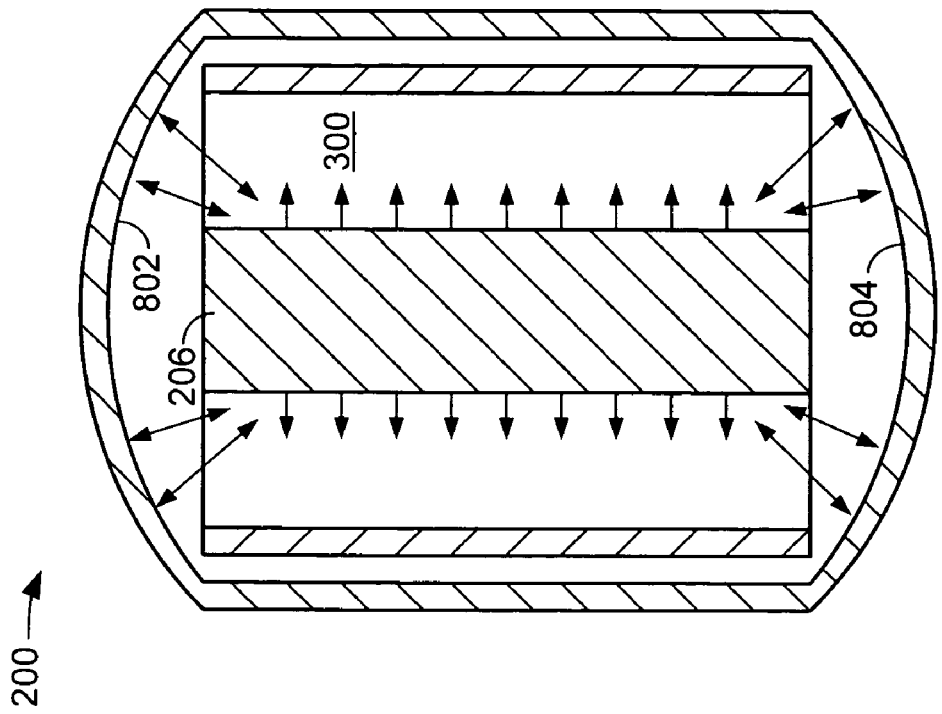
FIG. 14 is a cross-sectional schematic diagram illustrating an oven including interior surfaces having a reflective property.

FIG. 14 is a cross-sectional schematic diagram illustrating an oven 200 including interior surfaces having a reflective property. In an embodiment, the oven 200 includes reflective surfaces 802 and 804. The reflective surfaces 802 and 804 are configured to be reflective at the wavelength of the output of the radiant source 206. For example, the reflective surfaces 802 and 804 can be formed using a thin layer of gold so that stray radiant energy from the radiant source 206 is directed back toward the radiant source 206 and toward the analytic column 116.

Figure 15:
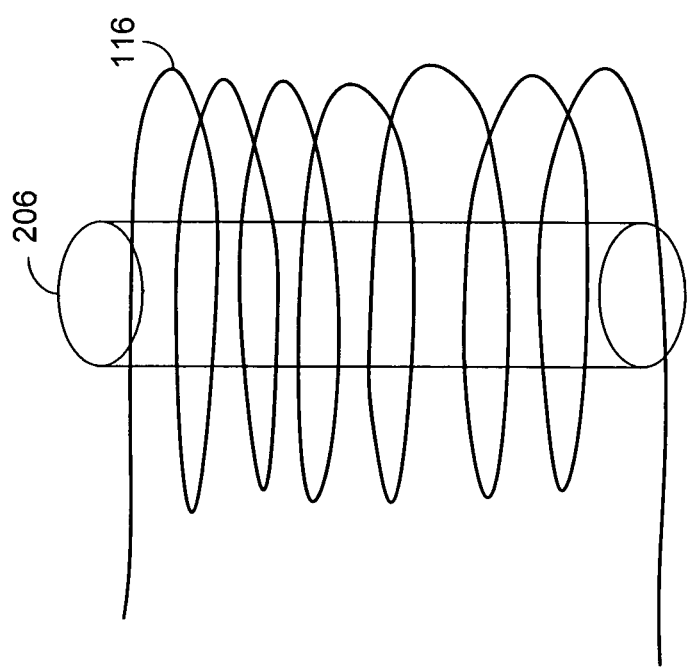
FIG. 15 is a schematic diagram illustrating a symmetrical shape for a cylindrical radiant source and an analytic column.

FIG. 15 is a schematic diagram illustrating a symmetrical shape for a cylindrical radiant source and an analytic column. The radiant source 206 is ideally as symmetrical as possible so that the geometry of the radiant source 206 is matched to the geometry of the target. In an embodiment the cylindrical shape of the radiant source 206 approximates the cylindrical shape of the wound analytic column 116.

Figure 16:
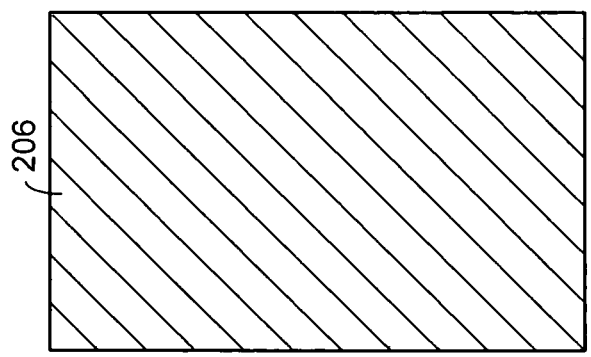
FIG. 16 is a schematic diagram illustrating a planar shape for a planar radiant source.

FIG. 16 is a schematic diagram illustrating a planar shape for a planar radiant source. The radiant source 206 is ideally as symmetrical as possible so that the geometry of the radiant source 206 is matched to the geometry of the target.

Figure 17:
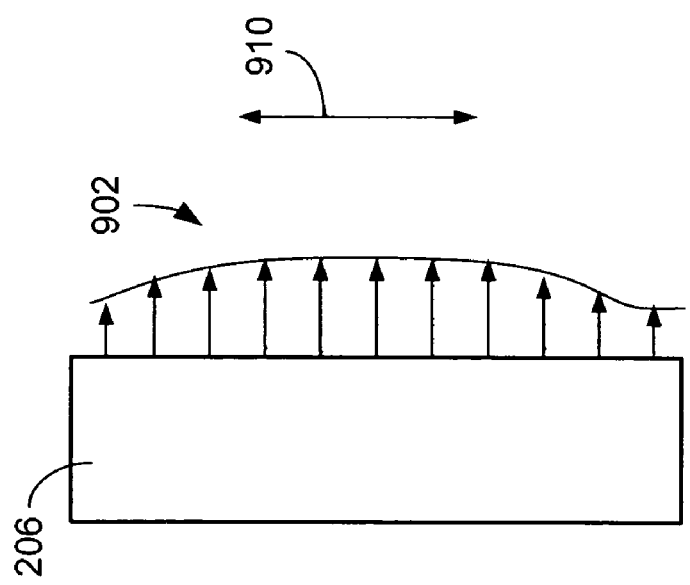
FIG. 17 is a schematic diagram illustrating an example radiation pattern for a radiant source.

FIG. 17 is a schematic diagram illustrating an example radiation pattern for a radiant source. The radiation pattern 902 exhibits a lower output at the edges than at the center. It is desirable to locate the target in the region indicated at 910 where there is an approximately uniform region of radiant energy. Locating the analytic column 116 in the region 910 contributes to uniform heating of the analytic column 116.

Figure 18:
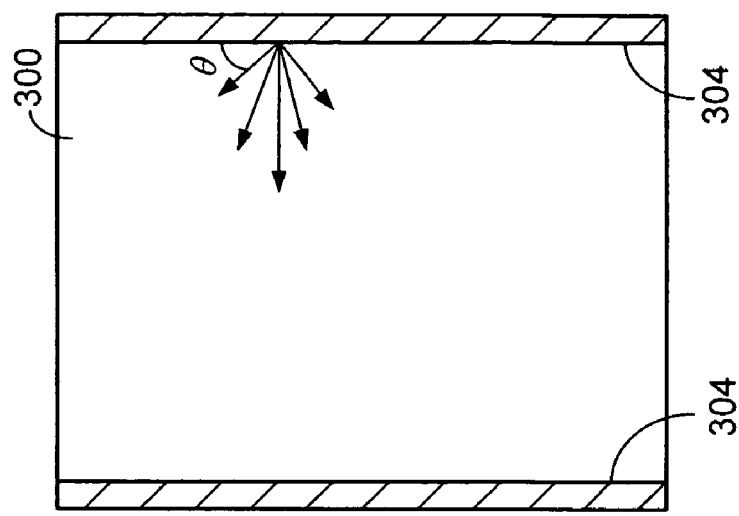
FIG. 18 is a schematic diagram illustrating an example radiation pattern received from a radiant source.

FIG. 18 is a schematic diagram illustrating an example radiation pattern received from a radiant source. The radiant source 206 is omitted from FIG. 18 for clarity. In this example, the radiant source provides a collimated light output, such as the output provided from a laser. Further, FIG. 18 includes an insert 300 for ease of illustration. However, the insert 300 can be replaced by an analytic column 116. The radiant energy that is imparted to the inner surface 304 of the insert 300 is imparted at an angle theta ($\theta$). Depending on the magnitude of $\theta$, the amount of energy absorbed by the inner surface 304 will change. In accordance with an embodiment of the invention, the proximity and relationship between the radiant source 206 and the target (in this example, the inner surface 304 of the insert 300) is designed to maximize the solar absorbtivity, $\alpha$ of the target. The radiant source 206 provides a radiation pattern and the analytic column 116 is located proximate to the radiation pattern so that an angle of incidence with respect to the radiation pattern and the analytic column 116 is consistent to maximize absorption of radiant energy emitted from the radiant source 206.

Figure 19:
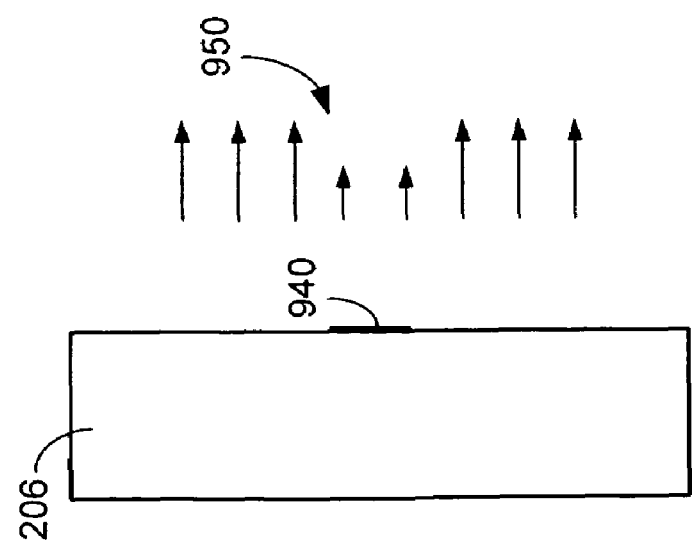
FIG. 19 is a schematic diagram illustrating an example of the effect of debris on the radiation pattern of a radiant source.

FIG. 19 is a schematic diagram illustrating an example of the effect of debris on the radiation pattern of the radiant source 206. As shown, a thermal gradient 950 is present in the radiant output by debris 940 located on the radiant source 206.

Figure 20:
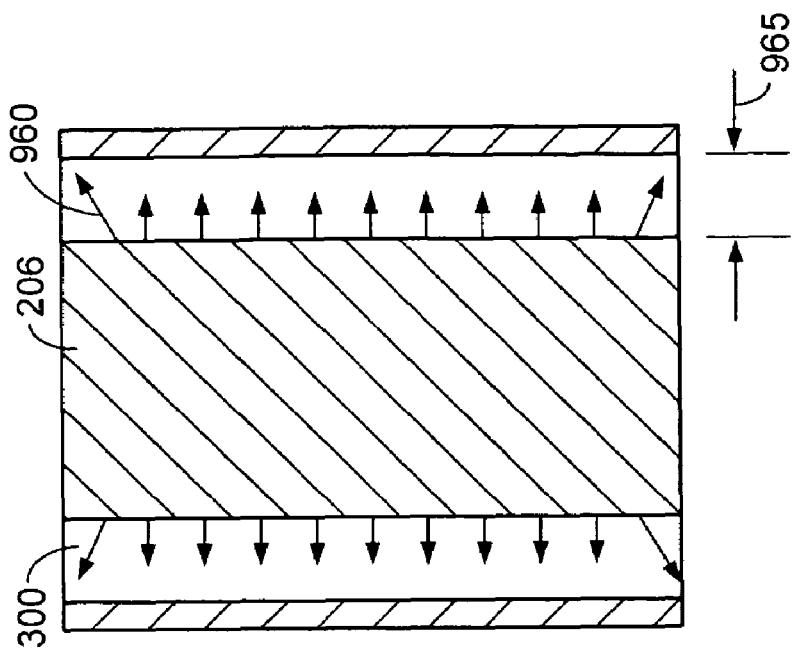
FIG. 20 is a cross-sectional schematic diagram illustrating an example of maximizing the size of the radiant source to minimize a gap between the radiant source and the target.

FIG. 20 is a cross-sectional schematic diagram illustrating an example of maximizing the size of the radiant source 206 to minimize a gap 965 between the radiant source and the target. In this example, the target is depicted as the inner surface 304 of the insert 300. However, the target can be the analytic column 116 in the absence of the insert 300. Minimizing the dimension of the gap 965 minimizes the occurrence of stray radiant energy 960 and maximizes the radiant energy impinging on the target.

The foregoing detailed description has been given for understanding exemplary implementations of the invention and no unnecessary limitations should be understood therefrom as modifications will be obvious to those skilled in the art without departing from the scope of the appended claims and their equivalents.

What is claimed is:

1. A gas chromatograph system, comprising:
a radiant source;
an insert located to receive an output of the radiant source; and
an analytic column wound on a concave surface of the insert so that successive coils of the wound analytic column are in direct contact with each other and exert an outward pressure on the concave surface of the insert such that the outward pressure minimizes a gap between the analytic column and the concave surface of the insert so as to minimize thermal gradients and maximize heat transfer to the analytic column.

2. The system of claim 1, further comprising a coating on the analytic column, the coating being absorptive of the energy emitted from the radiant source.

3. The system of claim 1, further comprising a coating on the analytic column, the coating being of uniform thickness and absorptive of the energy emitted from the radiant source.

4. The system of claim 1, further comprising a coating on the analytic column, in which the coating varies in thickness over the analytic column to compensate for temperature variation over the analytic column caused by natural convection.

5. The system of claim 1, in which the insert further comprises a uniform thickness coating that is absorptive of the energy emitted from the radiant source.

6. The system of claim 1, in which the radiant source has a first shape and the analytic column has a second shape, where the first shape approximates the second shape.

7. The system of claim 6, further comprising a filament in the radiant source, the filament being symmetrical with respect to the first shape.

8. The system of claim 1, in which the successive coils of the analytic column insulate each other.

9. The system of claim 1, in which the analytic column is wound into a shape in which the dimension of the wound analytic column in the direction of gravity is the smallest dimension of the wound analytic column.

10. The system column of claim 1, in which the radiant source comprises a structure configured to vary an output of the radiant source so that thermal energy imparted to the analytic column is varied to compensate for the temperature variation over the analytic column caused by natural convection.

11. The system of claim 1, further comprising a light diffuser located between the radiant source and the analytic column.

12. The system of claim 1, in which the radiant source provides a radiation pattern and the analytic column is located proximate to the radiation pattern so that an angle of incidence with respect to the radiation pattern and the analytic column is consistent to maximize absorption of radiant energy emitted from the radiant source.

* * * * *